(12) United States Patent
Smith

(10) Patent No.: US 6,482,362 B1
(45) Date of Patent: Nov. 19, 2002

(54) MEMBRANE FILTERED PIPETTE TIP

(76) Inventor: James C. Smith, 336 Harder Rd., Hayward, CA (US) 94544

( * ) Notice: Subject to any disclaimer, the term of this patent is extended or adjusted under 35 U.S.C. 154(b) by 69 days.

(21) Appl. No.: 09/625,227

(22) Filed: Jul. 24, 2000

Related U.S. Application Data

(62) Division of application No. 08/841,971, filed on Apr. 8, 1997, now Pat. No. 6,117,394.
(60) Provisional application No. 60/015,240, filed on Apr. 10, 1996.

(51) Int. Cl.$^7$ .................................................. B01L 3/02
(52) U.S. Cl. ..................... 422/100; 73/864.03; 422/101
(58) Field of Search ................................ 422/100, 101; 436/54, 178, 180; 73/864.03

(56) References Cited

U.S. PATENT DOCUMENTS

| | | | |
|---|---|---|---|
| 4,022,576 A | | 5/1977 | Parker |
| 4,267,729 A | | 5/1981 | Eddelman |
| 4,973,450 A | | 11/1990 | Schluter |
| 4,999,164 A | | 3/1991 | Puchinger et al. |
| 5,496,523 A | | 3/1996 | Gazit |
| 5,580,529 A | | 12/1996 | DeVaughn et al. |
| 5,697,522 A | | 12/1997 | Mayes |
| 5,833,927 A | * | 11/1998 | Raybuck et al. |
| 5,876,918 A | * | 3/1999 | Wainwright et al. |

FOREIGN PATENT DOCUMENTS

| | | | |
|---|---|---|---|
| JP | 10-288571 | * | 10/1998 |
| WO | 95/27797 | | 10/1995 |

OTHER PUBLICATIONS

Anonymous, "Pipette tip which aspirates without filtering and filters dispensed liquid," Research Disclosure (Emsworth, GB), Sep. 1993, pp. 586–593.

* cited by examiner

Primary Examiner—Jan Ludlow
(74) Attorney, Agent, or Firm—William Michael Hynes; Townsend and Townsend and Crew, LLP

(57) ABSTRACT

An apparatus and method of manufacture for a pipette tip having a membrane filter includes a pipette tip having an interior annulus for receiving an exterior perimeter of the membrane filter. A shear plate overlying the pipette tip defines an aperture having a dimension equal to the exterior perimeter of the membrane filter. A cylindrical punch has a path of motion for passing through the aperture in the shear plate to the interior annulus of the pipette tip. Membrane filter material is placed over the shear plate in the path of motion of the cylindrical punch. By the expedient of moving the cylindrical punch through the membrane filter material, the aperture in the shear plate, to the interior annulus of the pipette tip to place sheared filter material over the annulus of the pipette tip. Specific embodiments of pipette tips are illustrated including tips having a first filter for filtering material drawn into the pipette tip and second filters from preventing contamination of the pipette.

8 Claims, 11 Drawing Sheets

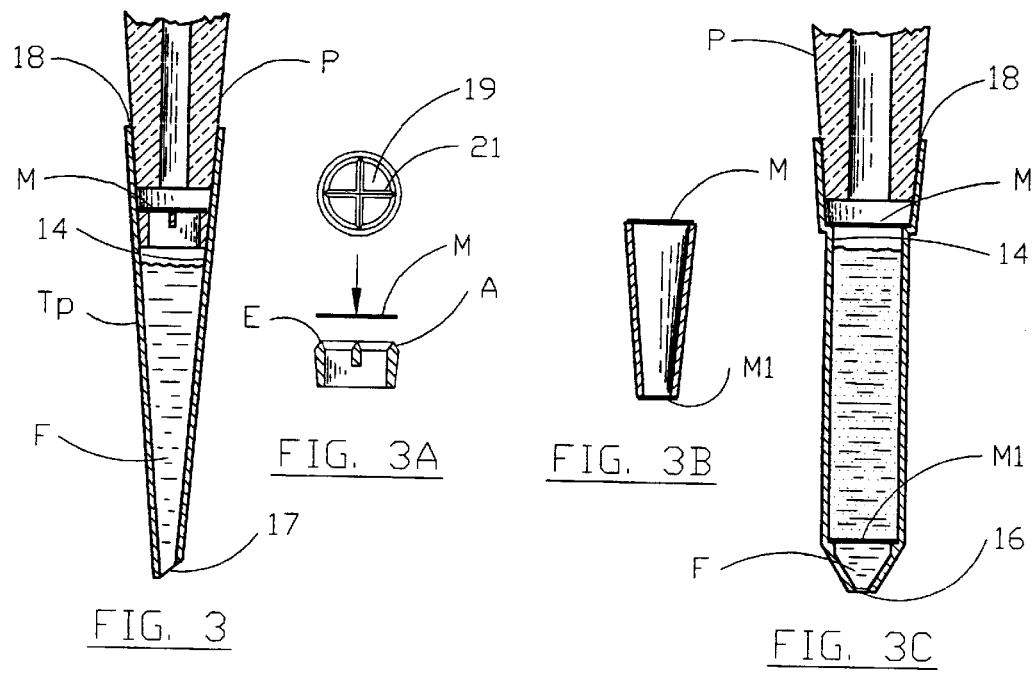
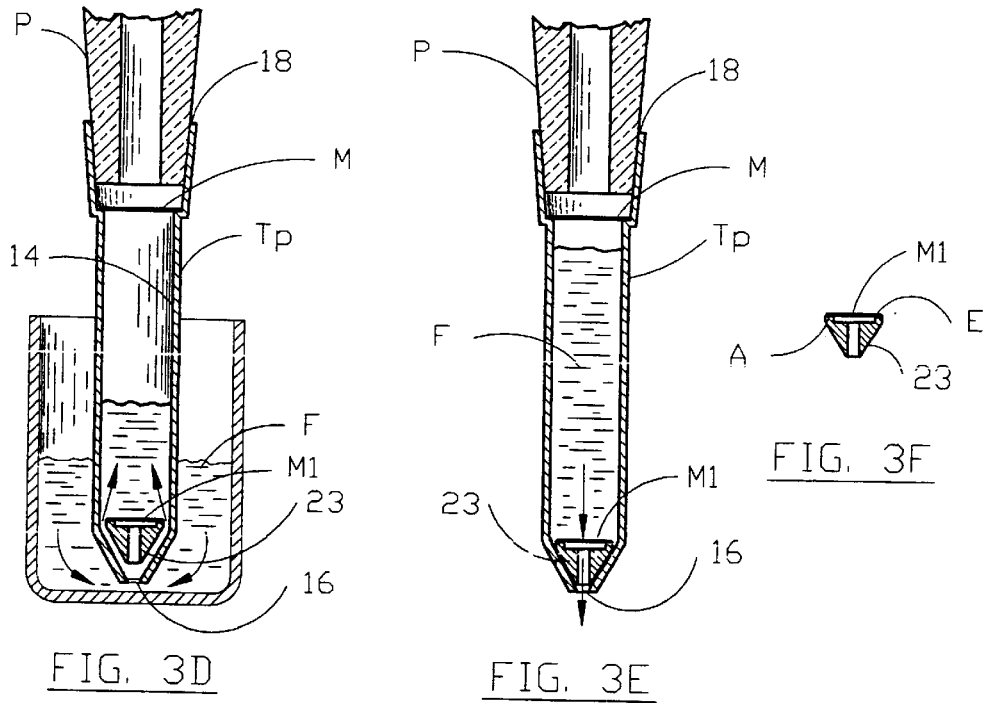

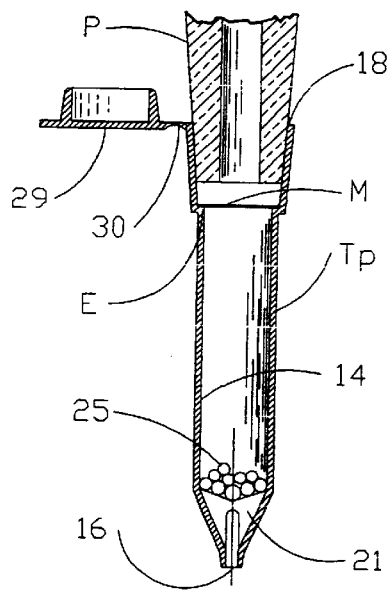
FIG. 3G
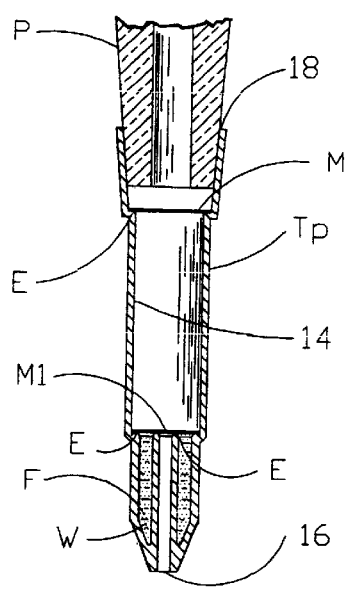
FIG. 3H
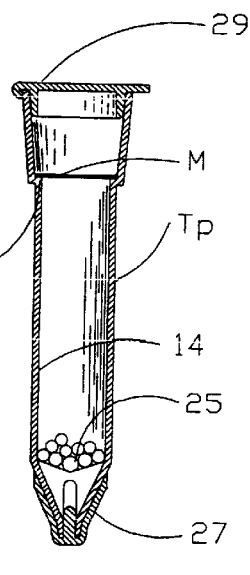
FIG. 3I
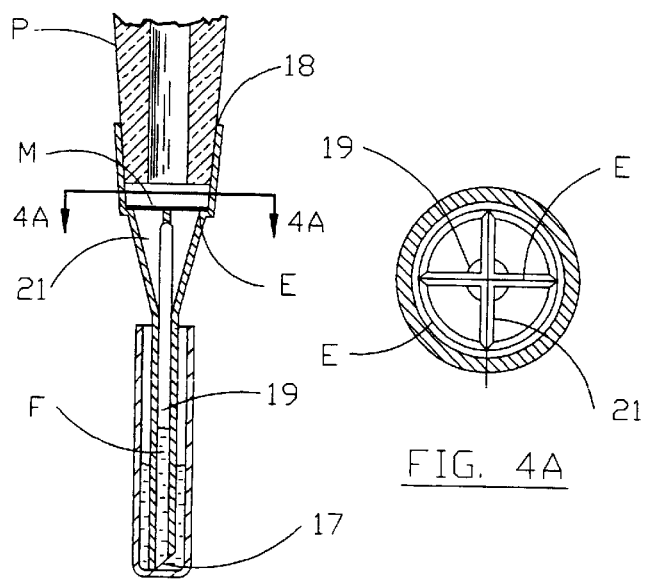
FIG. 4
FIG. 4A
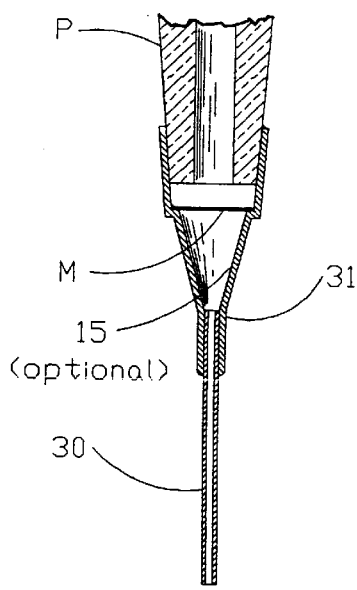
FIG. 4B

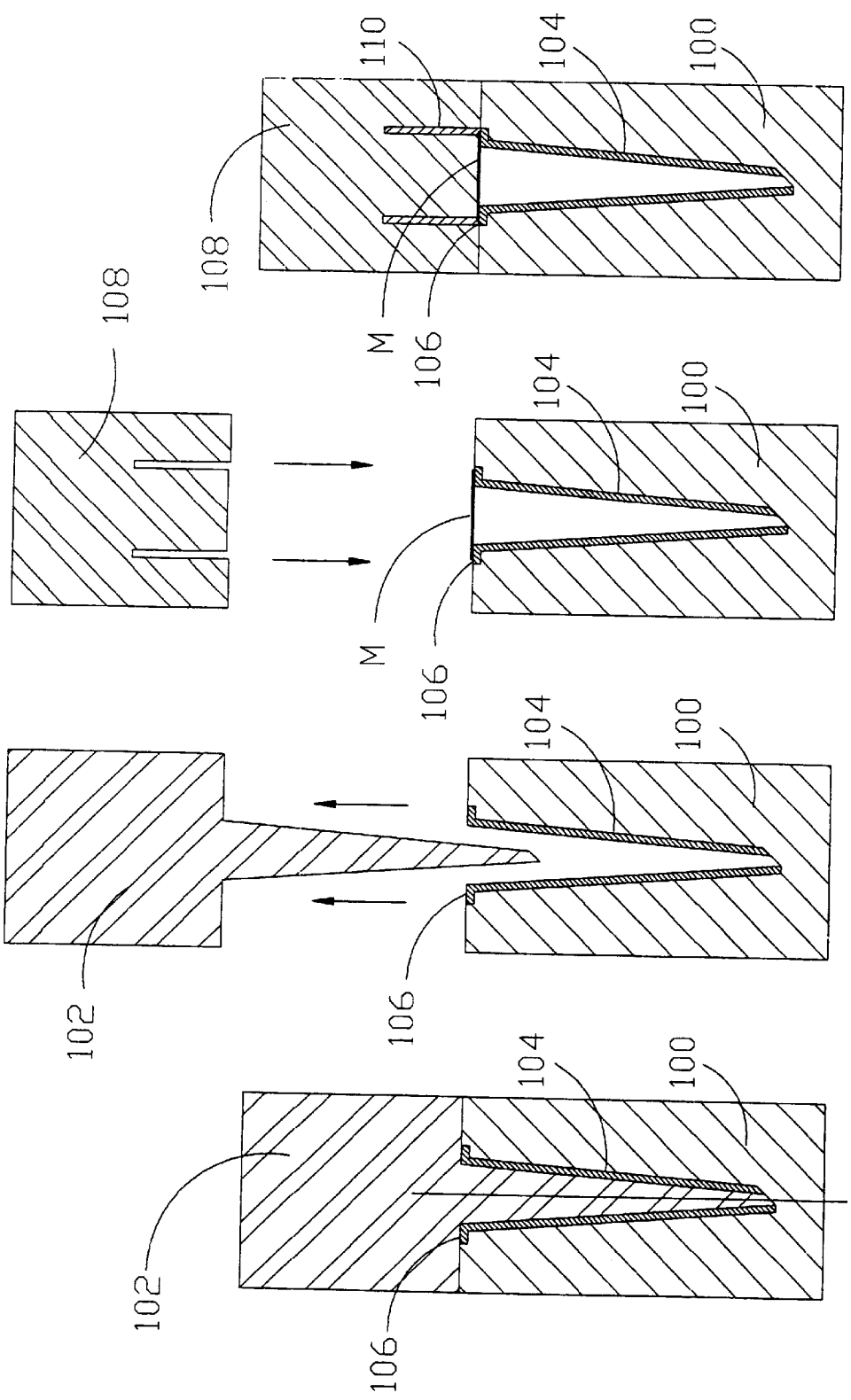

MEMBRANE FILTERED PIPETTE TIP

This application is a divisional of and claims the benefit of U.S. application Ser. No. 08/841,971, filed Apr. 8, 1997 now U.S. Pat. No. 6,117,394 which is a Continuation-in-part of Application No. 60/015,240, filed Apr. 10, 1996, the disclosure of which is incorporated by reference.

This invention relates to disposable tips for pipette devices. More particularly, a method of manufacture and a product of the method is disclosed for a mass produced pipette tip.

BACKGROUND OF THE INVENTION

Air displacement pipetters with disposable tips have been used in the medical industry for many years. The main reason for such continual acceptance comes from the fact that after each use the tip has traditionally been disposed of, thereby limiting the possibility of cross contamination between samples. However, because of the need to perform many tests from a limited account of sample quantity, polymerase chain reaction (PCR) was developed. PCR (covered under U.S. patents issued to CETUS Corporation), provides a method with which to produce many copies of a specific nucleotide sequence from a minute quantity of DNA.

Unfortunately, false signals can be generated following PCR amplification due to cross-contamination accuracy during carry-over between existing tips and air displacement pipetters. As the scrutinizing of these and many more tests have become more demanding, the need to eliminate any and all cross contamination is imperative. Even the smallest amounts of particles left behind on the barrel of the pipetter from previous tests can invalidate, or skew the evaluations of new test samples, causing hours or even days of laboratory research to be wasted. These errors could be contributed to operator use (which often causes splashing of the sample) or the sample could aerosol during aspiration of the fluid sample, or the fluids contaminated gases can flow into the tip upward into the calibrated barrel in the form of air borne contaminates.

The filtered disposable pipette tip was developed to help prevent such problems. However as shown below, the advantages of the existing designs do not meet the more stringent requirements for test evaluations of today's medical requirements.

Existing Filter Tips

U.S. Pat. No. 4,999,164 by Puchinger, U.S. Pat. No. 5,156,811 by White, U.S. Pat. No. 5,364,595 by Michael Smith and U.S. Pat. No. 5,496,526 by Gazit all disclose a filter tip which contains a plug of porus material frictionally engaged within the liquid chamber of a standard pipette tip. Referring to FIG. 1, a simplified view of pipette tip Tp is illustrated. Pipette tip Tp defines frustum shaped interior cavity 14 having apex end 16 opening to receive fluid F to be pipetted and truncated base 18 is exposed to receive pipetter barrel P (only partially shown) in a wedge type fit.

Plug filter N is utilized. Typically, plug filter N is wedged into pipette tip Tp. This is done on an individual basis.

By taking existing disposable pipette tips and installing a porous filter medium into the tip itself, the existing product now provides a barrier between the incoming sample and the calibrated barrel of the pipette (as shown in FIG. 1). This barrier is constructed to block passage of aerosols while permitting gas to flow through its pores. If the liquid contacts the plug, as noted by White, the particles of the plug will expand and completely block gas or liquid flow. This does help to prevent the possibility of some cross contamination between samples when disposable tips are exchanged.

Disadvantage

1. Existing filter media used in the previously mentioned applications are porous plastics (such as made by Porex) with a preferable pore size in the order of 25–40 microns, yet many tests require particulate retention below 0.6 microns to be effective.
2. The actual filter mass necessary to maintain the interference of the fit also reduces the amount of calibrated fluid volume designed to be held by the fluid tip. Not only does this not maximize the efficiency of the tip, but it poses the potential for an error to occur when the user must account for this problem by selecting a larger tip. This new tip may or may not fit the tube or receiving container the user wishes to access, (i.e., a 250 $\mu$l tip may only hold a volume of 150 $\mu$l after the filter medium is installed as shown in FIG. 1).
3. As noted by White, when fluid does contact the plug the filter tip, its contents must be discarded. However, in cases where there is minimal sample material or no other sample available, this feature is disastrous because of the need to recover the sample locked within the tip.
4. The filter mass also reduces the air flow of the pipetter and thus effects the calibrated volume of fluid which is drawn into the tip. Back pressure and flow rates are essentially proportional to material thickness. Thus, assuming the same pore size, the pressure drop would double when the material thickness doubles, (i.e., if 0.060 thick filter had a 8 psi pressure drop, then a 0.120 thick filter would be 16 psi and a 0.240 thick filter would be 32 psi). Average existing filter media range from 0.12 to 0.25 inch thickness.
5. Cost is a major factor in any disposable, but $100–$125 per thousand is very high due to the fact the existing filters must be manufactured and installed individually.
6. Existing pipetters are designed and calibrated without the use of this filter barrier within the tips. To maintain the original accuracy and precision specification of the pipetter, a minimum pressure drop is required. Thus, these prior art filter tips sometimes require the re-calibration of the pipetter to accommodate this filter mass.

It will also be understood that pipette tips having membrane filters are known. See Edelmann U.S. Pat. No. 4,267,729 and the prior art illustration shown in FIG. 1A.

Referring to FIG. 1A, pipette tip Tp1 is illustrated defining frustum shaped interior cavity 14 with apex end 16 showing drawing fluid F and truncated case 18 attached to pipetter P (partially shown). Annulus A includes flat surface 20 extending normally to axis of symmetry 22. In Edelmann U.S. Pat. No. 4,267,729, conventional fastening, as by the use of adhesives, fastens membrane filter M to annulus A.

In Edelmann U.S. Pat. No. 4,267,729, membrane filter M has a special purpose. It is used as a stop for pipetted material. Specifically, in Edelmann, the volume delimited between membrane filter M and apex end 16 amounts the measured amount of fluid to be pipetted.

U.S. Pat. No. 4,461,328 by Kenny also discloses a pipetting device that comprises one or more pipette tubes to which a hydrophobic filter paper is secured. It also restricts the rise of an aqueous liquid in each tube, by the use of its hydrophobic paper similar to Edelmann, by allowing the passage of air from a liquid mass.

Disadvantages

1. In the above mentioned configurations, the devices are quite susceptible to plugging by particulate masses in the fluid samples. One example would be fibrin contained in blood samples which is a fibrous blood protein used in the clotting process.
2. Contamination is again a major concern when the liquid of any sample comes in contact with the filter medium or possibly the adhesives used for the attachment of the filter.
3. Fluid contacting the filter medium will create a meniscus, attaching itself to the medium, depending on the fluid's viscosity and surface tension of the medium during its dispensing cycle. This will give rise to inaccuracies in the precision and accuracy of the volumes dispensed.
4. As with the porous plastic filter described by U.S. Pat. No. 5,156,811, the filter media of the above patents are primarily hydrophobic in nature and are only concerned with preventing fluids to pass the filter barrier while allowing gases to flow through. These gases, however, can contain air borne contaminants which freely enter the pipetter barrel through normal operation of the suction and dispensing cycle of the pipetter. Upon exchanging a new filter tip the contaminants may again flow from the contaminated barrel though the filter media and into the dispersed fluid sample.
5. Another major objection is the difficulties and relative high cost associated with the manufacturing of these products. Liquid pipetting requires both high precision and accuracy of liquids dispersed within plus or minus 0.5% for some tests. Devices such as these have proven to be quite difficult to fabricate because of the close tolerances and multi-cavity tooling required in the medical disposable marketplace.

SUMMARY OF INVENTION

A method of manufacture for a pipette tip is disclosed having a membrane filter. A pipette tip is provided having an interior annulus for receiving an exterior perimeter of the membrane filter. A shear plate overlying the pipette tip defines an aperture having a dimension equal to the exterior perimeter of the membrane filter. A cylindrical punch having a path of motion for passing through the aperture in the shear plate to the interior annulus of the pipette tip is provided. Membrane filter material is placed over the shear plate in the path of motion of the cylindrical punch. By moving the cylindrical punch through the membrane filter material and the aperture in the shear plate to the interior annulus of the pipette tip, a sheared filter material may be placed over the annulus of the pipette tip. An improved pipette tip results.

This disclosed manufacturing technique is capable of producing improved pipetter designs, which are generally described hereafter.

It is the object of this invention to improve a pipetting device which is of the kind described before. Today's requirements for liquid handling filtered pipette tips require specifically designed sterilizing filter membranes capable of retention rates down to 0.1 µm for protection against contamination form bacteria, DNA fragmentations, infectious organisms, fungi, blood borne contaminates, hazardous particulates and more. These filter membranes are absorbent or covalent and use electrostatic, ionic or oleophobic mechanisms for binding particulates, with retention rates of more than 99.99% for delivery of ultrapure or sterile air, unlike existing art.

Filter membranes such as Versapor R from Gelman sciences or the Durapel membranes from Millipore Corporation meet these stringent requirements. These and many new membranes are specifically created to be chemically inert and capable of withstanding high temperatures associated with autoclaving and other forms of sterilization such as Ethylene Oxide and gamma irradiation. It is also the object of this invention to have the ability to create a filtered pipette tip which is packaged and sterilized in conventional rack packaging for the end user.

Substantial advantages are afforded by the use of such filter membranes, because the flow of gas or liquid is subjected to different influences, which depending on the fluid and gas can be adapted to different substances (i.e.: specific bactericidal, virucidal or fungicidal actions) creating an ultrapure or sterile environment for elimination of all potential contamination.

The filter membrane will also be effective in two directions so that contamination of the interior of the pipetter above the filter membrane will be prevented as well as back-contamination of the sucked fluid from the gases dispensed by the pipetter plunger.

It is a further objective of the invention to provide a device highly resistant to plugging as well as other attributes that will become more apparent with the following description and method of tip manufacturing.

One embodiment having a frustum shaped interior is provided with an interior annulus for receiving a membrane filter. The interior annulus defines a raised energy director inset from the wall of the frustum shaped interior of the pipette. In manufacture, membrane filter material is serially dispensed over a shear plate defining punch holes. Underlying each punch hole, a rack positions individual pipette tips for receiving the punched and separated membrane filters. Hot cylinders equipped with or without vacuum overlie both the defined punch holes and the underlying pipette tips. Installation of the membrane filter includes passing the heated cylinders through the membrane material to shear the membrane filter at the punch holes in the shear plate. Upon such shearing, the vacuum apparatus on each cylinder is actuated to carry the sheared membrane filter material from the shear plate to the annulus interior of each pipette tip. The heated cylinders carrying the membrane filters continue downward to the interior pipette annulus into contact with the energy director at the annulus. Attachment.of the membrane to the annulus occurs at the energy director. Thereafter, vacuum is released, the hot cylinder retracted, and the filter membrane incrementally advanced for the next sequential operation. Extension of the membrane filter installation apparatus and process is disclosed for other embodiments and for multiple pipette tips.

One major advantage is the results that come from the use of HEPA (High Efficiency Particulate Air Filters) biologically inert microfilter membranes. HEPA filters are classified (per ASTM: D2988-71) as retaining greater than 99.97% of a 0.3 µm DOP (Dioclylphthalate) aerosolized contaminates. This is the standard for delivering sterile, particulate-free air under normal applications. Unlike filters used in existing filter tips, this membrane material is manufactured to high quality standards in the form of thin sheets or rolls on a microscopic scale, which makes them superior to other porous materials. By controlling the material specifications of this thin membrane sheet (i.e., Nitrocellulose, Cellulose Acetate, Nylon, PTFE, etc.) any number of factors can be considered in pipette filter tip design. For example pore size (0.05 to 0.3 $\mu$m), flow rate, throughout, autoclavable, hydrophobic, strength, gamma irradiation sterilable, chemical compatibility, temperature requirements and other factors can be used in the development of any desired filter for any type environment, while providing the utmost in cross-contamination protection. This thin membrane and how it is incorporated in this disposable plastic tip solves the major disadvantage of prior art while most importantly providing greater levels of accuracy, precision and reproducibility than ever before while being less expensive to manufacture.

As shown in FIGS. 2 and 2A, the thin membrane filter material is heat or ultrasonic sealed onto the shoulders of the plastic disposable tip. Its location is such that it is below the barrel of the pipetter, yet between it and the calibrated fluid within the tip. The mechanical size of the thin membrane does not affect the tip from drawing up its maximum fluid capacity while maintaining the minimum outside tip configuration unlike existing filter tips. Existing filter tips require a large mass of filter material (as shown in FIG. 1). This creates a larger air space within the tip and can ultimately lead to less accurate liquid dispensing because of the back pressure between the upstream and downstream sides of the filter when the pipetter is drawing fluid into the tip. However the thin membrane offers less restrictive flow of air, thus creating more accurate dispensings, (similar to non-filter tips with which pipetters are calibrated).

Because the filter membrane is so thin, (i.e.: 100 to 200 microns) the plastic tips can be manufactured as small as the maximum volume of fluid they hold. This is very important because some containers (i.e. PCR test tubes, centrifuge tubes, etc.) have minimum size openings which do not allow the use of larger sized tips (as is currently required using existing filter tips).

FIG. 2A shows a tip detail for the heat sealings or ultrasonic weld energy director necessary to attach the filter membrane to the disposable tip. The shoulder seal width and height are very important and range from 0.04 to 0.08 wide by 0.02 to 0.05 high. The upper chamber is designed for mating with the correct pipetter barrel interface.

In another embodiment, FIG. 3 utilizes a standard pipette tip for attachment of a matting tapered cylindrical tube as shown in FIG. 3A in a press fit relationship. This cylinder with or without internal ribs 21 can be manufactured with energy directors E similar to FIG. 2A for attachment of the filter membrane. FIG. 3B shows another desirable embodiment, where filter membranes are attached to both ends of the tapered cylinder. The lower filter M1 being hydrophilic allowing fluid to pass through it while the upper filter membrane M may be hydrophobic but would only allow sterile gases to pass. In this embodiment, the lower membrane M1 could be used as a fluid filter. One example of its use would be where the filter media would allow plasma to flow through while preventing red blood cells to pass when working with blood samples. Another variation, the M1 membrane, could be impregnated with substances that would react to the sample as the fluid flows through the filter, combining particular chemicals with the fluid samples for testing or evaluation purposes. It will also be possible to automate filter attachment and insertion capability by molding these cylinders in configurations similar to the normal 8×12 matrix (0.354 center to center) or 8, 12, 24, 48 or 96 at one time for high volume production.

In a preferred embodiment, FIG. 3C comprises the upper and lower filter membranes sealing attached to the pipette tip without the need of the tapered cylindrical part. The M1 filter membrane is positioned above small orifice end item 16, to increase its surface area to help minimize clogging and back pressure problems.

In another embodiment, FIG. 3F shows the lower filter membrane M1, being sealingly attached to the top of a tapered plastic cone 23, with an opening through it. FIG. 3D shows the location of cone 23 within the tip when unfiltered fluid is being drawn around the cone 23 and into sample cavity. FIG. 3E shows the conical side walls of cone 23 mating and sealing with the internal sidewalls of the pipette tip, thus directing the unfiltered sample fluid through filter M1 creating a filtered fluid discharge of the sample. This again could be used to filter the sample fluid or introduce dry reagents into the liquid sample that would react with the sample causing a color change, reflectance or electrical conductivity. An example of this might be as a sample of urine or serum is dispensed it wets out and moves through the porous matrix M1 and it solubilizes one or more reagents that have been previously deposited into the membrane Ml bed volume. This would allow the manufacturers to ship its tips preloaded with many or all of the reagents that would be required to complete the analysis or test requirements.

Cone 23 with membrane M1 could also be used to capture particulates in the fluid sample. This would expedite the separation or binding of components in a one step operation. Whereas, upon the dispensing of the sample fluid, the cone 23 with membrane would be removed from the tip cavity and analyzed by eye or with appropriate instrumentation for the particulates that have bonded onto the filter membrane.

Another variation would be to fill the cavity of cone 23 with dry reagents that would also mix with the sample as it pushes it out during the dispensing cycle. Another variation, as shown by FIG. 3G, would be to pelletize the reagents, item 25, or other additives and place them in the lower sample volume chamber to be dissolved and mixed with the fluid sample in the suction and dispensing cycles for performing various testing and diagnostic procedures. In accomplishing the same results, the tip can be pre-coated with a predetermined amount of chemical or biochemical agents, item 15, on its interior walls below the membrane M before it is installed. This would mix with a known quantity of incoming fluid to complete a particular test reaction.

Another variation, as shown by FIG. 3H, may be that a calibrated well would be created below the M1 filter that had been impregnated with a specialized mixture of reagents, which will react with the test sample causing a color change which could be seen though the pipette after the fluid is dispensed. It is also noted that these membranes may be impregnated with these substances in different patterns, as could be shown by a donut shaped pattern in the last example, where the center may be open to increase fluid flow. All of these variations would promote faster, more accurate and less expensive products than now exist in the marketplace.

With the addition of dry reagents or reactants to the inside of the tip cavity, it becomes beneficial to provide a protective cap 27, made from flexible chemically inert plastic, that would snap or frictionally fit over apex end 16, providing a hermetic seal for reagent protection during storage or shipment. The cap 27, could also be used in conjunction with tip cap 29, that would be molded with tip tp and connected via living hinge 30, to store a predetermined amount of known chemicals which, optionally, can be maintained sealed until use.

It is an object of this invention to provide a method, apparatus system and reagent coated pipette tip which permits the introduction of a predetermined amount of fluid into the tip cavity having a pre-introduced known quantity of dried reagent allowing it to contact and mix to perform a particular diagnostic test or other reactions which may require precise amounts of reagents.

It is another object of this invention, to provide a filter membrane tip including a reagent-bearing filter to permit treatment of a solution passing therethrough. The impregnated filter or reagent coating may contain an indicator chemical to change color when the solution mixes with it, thereby signaling that the reaction treatment has taken place. It is understood, that after the predetermined fluid is drawn within the tip cavity, that the protective cap 27, can be installed for storage or further evaluation of the reacted solution within the tip. With the addition of the protective cap, the pipette tip, which is normally used as a fluid transferring device, has now become a storage container with vented membrane top M, after it is ejected from the pipetter barrel and placed in an appropriate holder.

It is also an object of this invention, to provide for complete containment of the fluid within the tip cavity with the further addition of tip cap 29, as shown in FIG. 3I. This concept eliminates the need to transfer the sample solution from one microtube or vial into another device for ultra-filtration or into a separate reaction microtube for analysis. It also saves the very important fluid, which is known to be lost in any transfer using a pipette tip because of the material left behind on the inside surface of the transferring pipette tip due to the surface tension of the plastic. In many instances, when transferring very small amounts of fluids, these left behind droplets are so great that they skew the test results costing both time and money. By using the tip itself, as not only a means to add reagents or reactants to solutions, but also to provide a means for storage of the mixed solutions, we have created a simple and less costly method by which fluid can be analyzed.

It is also understood that the protective cap may be molded into the bottom of any storage or testing rack in any multiple (i.e., 8, 12, 24, 96, etc.) to reduce the number of piece parts, time of assembly and total overall costs.

In another preferred embodiment, FIG. 4 shows an alternate tip design that would allow the use of a very small bore size (i.e., 0.010 to 0.060) in conjunction with the use of the thin filter membrane material. FIG. 4A shows a section view describing the wall formed between the attachment diameter and the liquid sample chamber. This wall would incorporate holes 19 to allow gases to flow through. It would be constructed using ribs 21 with additional energy directors on its surface to provide additional support for fragile filter membranes. These tips would be used to draw very small amounts of fluid samples (i.e., 0.5 to 50 microliter). This design provides for a very small outside configuration so that it may be used to access very small containers. It also provides for an increased area under the filter membrane to reduce the back pressure and increase the airflow of the filter membrane to insure more accurate dispensing in the smaller fluid disposable tip. This is of particular need in the PCR area where very small amounts of samples are used. In addition apex end 17 is angled preferably between 15 degrees to 60 degrees to allow the end to contact the bottom of the container while still providing an opening for liquid withdrawal, unlike existing art. This allows the tip to maximize the amount of sample that is capable of removing from its container. This is of the utmost importance when valuable or limited samples are used. It also eliminates the problems of plugging the end of the tip with the bottom of the container which also would affect the accuracy of the fluid sample being withdrawn. It is understood this concept can be incorporated into any of the proposed tip configurations and would be especially beneficial in the multichannel pipetters and useful in automated pipetting machinery that may require the addition of coated reagents.

Another variation of the small bore tip utilizes the addition of a pipetting or syringe needle 30 that would be used to form the lower portion of the pipette tip as shown in FIG. 4B. This configuration is suitable for transferring fluids into small openings or when a surface must be pierced, in order to transfer or withdraw the sample, as is the case with some microcentrifuge tubes. The needles may be configured with 90-degree blunt ends, beveled or domed ends with a side hole to minimize septum damage upon insertion. In most cases, the needle will be manufactured from stainless steel for its piercing strength. However, some instances could arise where chemical resistance and not strength become more important. In these cases, small pipette tubing would be manufactured from chemical resistant material such as glass, teflon or PEEK. In all cases, the needles or chemically inert tubes must be hermetically sealed to the hub 31 by means of insert molding, press fit, adhesive bonding or other known means of attachment.

Another major advantage of the membrane filter is its ability to be manufactured in void volumes of 75 to 85% compared to porous plastics which typically are 35 to 65%. An increase in void volume results in higher flow rates at the same pressure and mean pore size which is beneficial to the accuracy and precision of the air displacement pipetter. Membranes also offer consistency of manufacturing and structural homogeneity on a microscopic scale, unlike existing porous materials used in the disposable tip industry today.

The thin filter membrane sheet can be manufactured in various sheet sizes or by the roll. FIG. 5 shows how these filter tips might be manufactured least expensively. This figure shows a cross-section of 8 tips loaded in a tray. It could also represent an 8×12 matrix of tips similar to the typical tip tray used in the industry (i.e., 0.354 center-to-center). In either configuration, or variation thereof, the filter membrane is positioned over the disposable tips. The punch is created with small vacuum holes to hold this filter paper in position after it has been sheared (FIG. 6) from the roll, until such time as it is bonded (heat welded) to the plastic tip (FIG. 7). The punch would then release vacuum and return to its starting position (FIG. 5). The filter paper would index to its next location to prepare the filter media for the next ray of tips.

BRIEF DESCRIPTION OF THE DRAWINGS

FIG. 3 is a cross section of a prior art pipette tip with a membrane filter cylinder press fit into its interior;

FIG. 3A is a perspective view of the cylinder and cross section thereof;

FIG. 3B is a cross section of a tapered cylinder with upper and lower filter membranes;

FIG. 3C is a cross section of a filtered membrane pipette tip with upper and lower filters;

FIG. 3D is a cross section of a filtered check valve tip in the suction cycle;

FIG. 3E is a cross section of a filtered check valve tip in the dispensing cycle;

FIG. 3F is a cross section of the cone shaped check valve;

FIG. 3G is a cross section of a filtered pipette tip with pelletized chemicals and protective cap;

FIG. 3H is a cross section of a filtered well pipette tip;

FIG. 3I shows pipette tip with protective cap and tip cap being used as a storage container;

FIG. 4 is a cross section of a micro-pipette filter tip with angled apex end;

FIG. 4A is a section taken just above the filter support of the micro-pipette illustrated in FIG. 4 (without filter installed);

FIG. 4B shows metal needle or tubing attached to plastic hub for mounting to a pipette barrel;

FIGS. 17A–17D are a cartoon series in side elevation section with FIG. 17A illustrating the injection molding of the lower conical section of the pipette tip, FIG. 17B illustrating the withdrawal of a portion of the mold section of FIG. 17A, FIG. 17C illustrating the placement of the membrane and the overlying exploded relations of a second and substituted injection mold; and, FIG. 17D illustrating the final molding of the pipette tip.

DESCRIPTION OF PREFERRED METHOD

The following specification is taken from my disclosure document entitled "Hydrophobic Membrane Filter Pipette Tip" filed and dated Jul. 20, 1994, U.S. Pat. No. 358,082, in the United States Patent Office.

Figure 1:
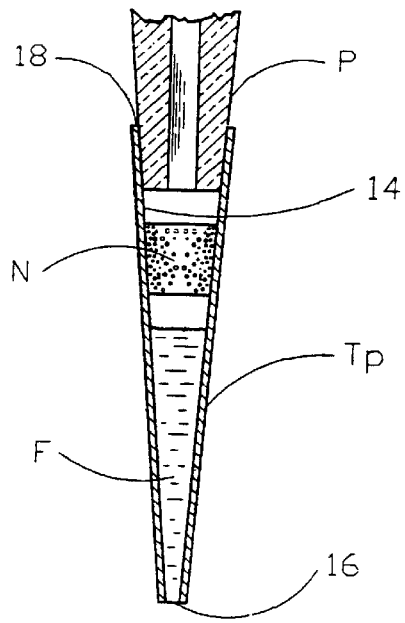
FIG. 1 is a cross section of the prior art illustrating a filter plug within a pipette tip.
Figure 1A:
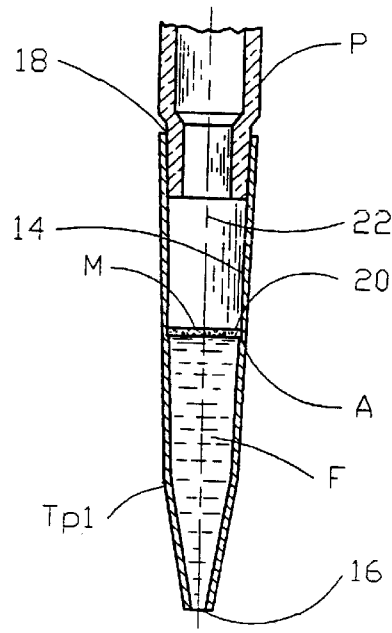
FIG. 1A is a cross section of the prior art illustrating a membrane filter installed on a conventional annulus.
Figure 2:
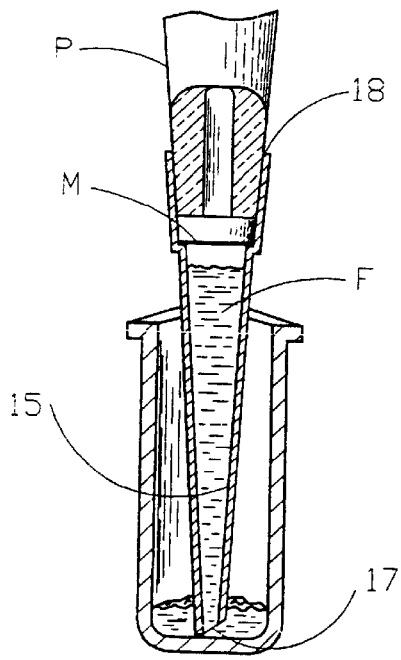
FIG. 2 is a cross section of filter membrane pipette tip with angled apex end.
Figure 2A:
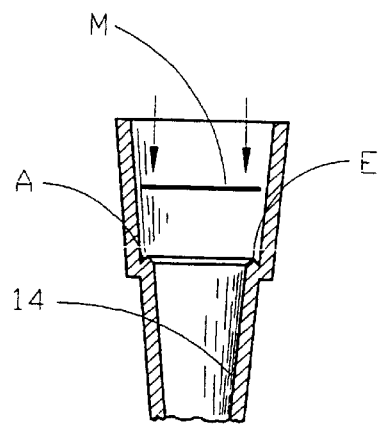
FIG. 2A is a perspective view of the membrane filter being placed on the energy director.
Figure 5:
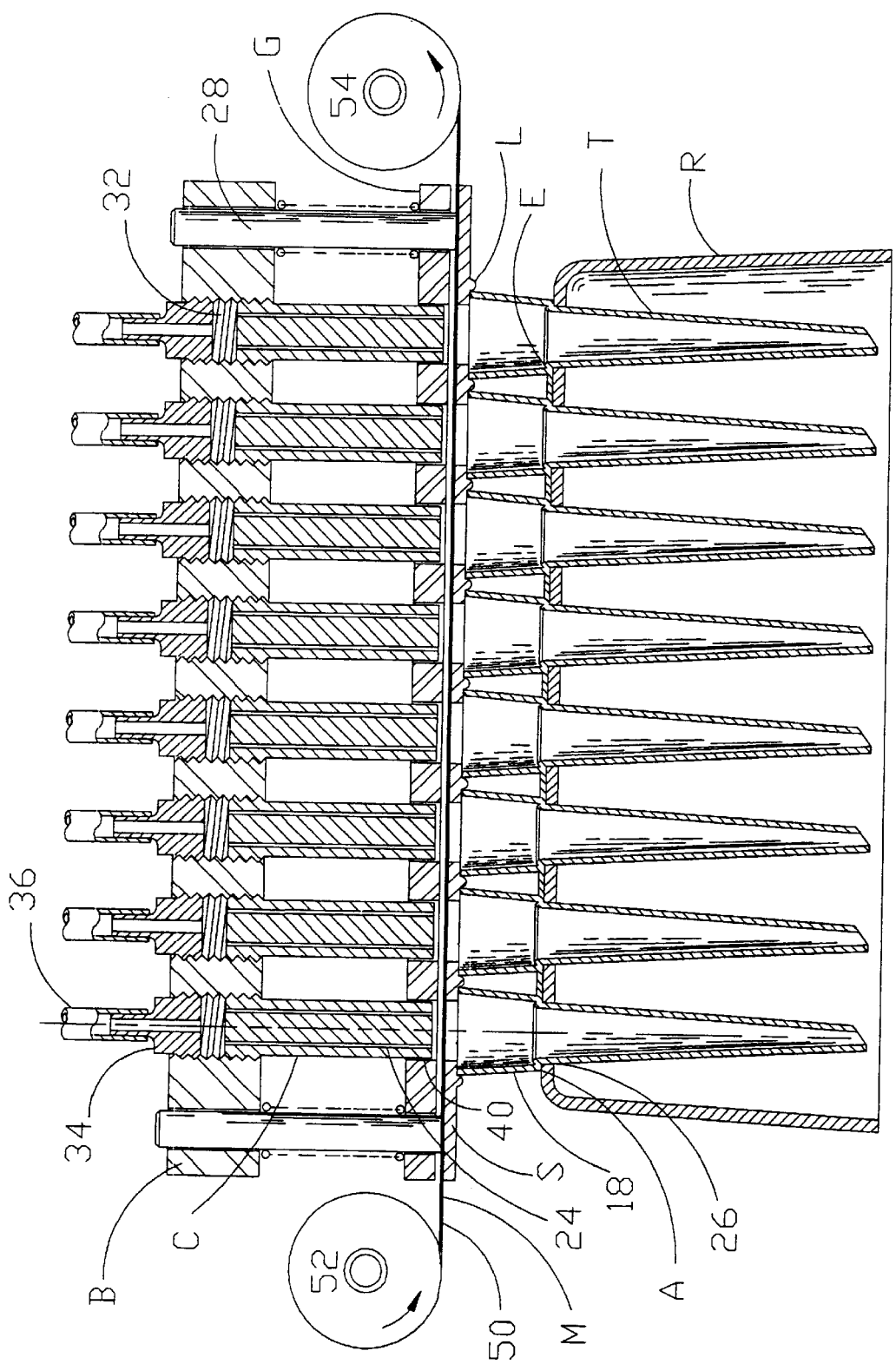
FIG. 5 illustrates the apparatus for manufacture illustrating a group of pipette tips with overlying membrane filter material positioned on a shear plate with punching of the circular membrane material about to occur.

As shown in FIGS. 2, 3 and 4, I have improved the existing filter tip designs by incorporating a thin filter membrane at energy director E. This design is unique because it not only offers many advantages to the prior art but can be produced in mass quantities using filter sheet membranes (as shown in FIG. 5) in trays up to 96 at a time. It is to be noted that membranes are usually formed in a continuous linear process so their physical properties are very uniform. Regarding placement of membrane filter M to energy director E on annulus A and or ribs 21. Such placement is illustrated in FIGS. 2, 3 and 4. Specifically, heated cylinder C carriers membrane filter M in its path to seat membrane filter M at energy director E on ribs 21 and/or at its periphery to annulus A at energy director E. Immediately before heated cylinder C places membrane filter M, the membrane filter M is held to the tip of heated cylinder C by vacuum communicated to vacuum channels 24.

Figure 6:
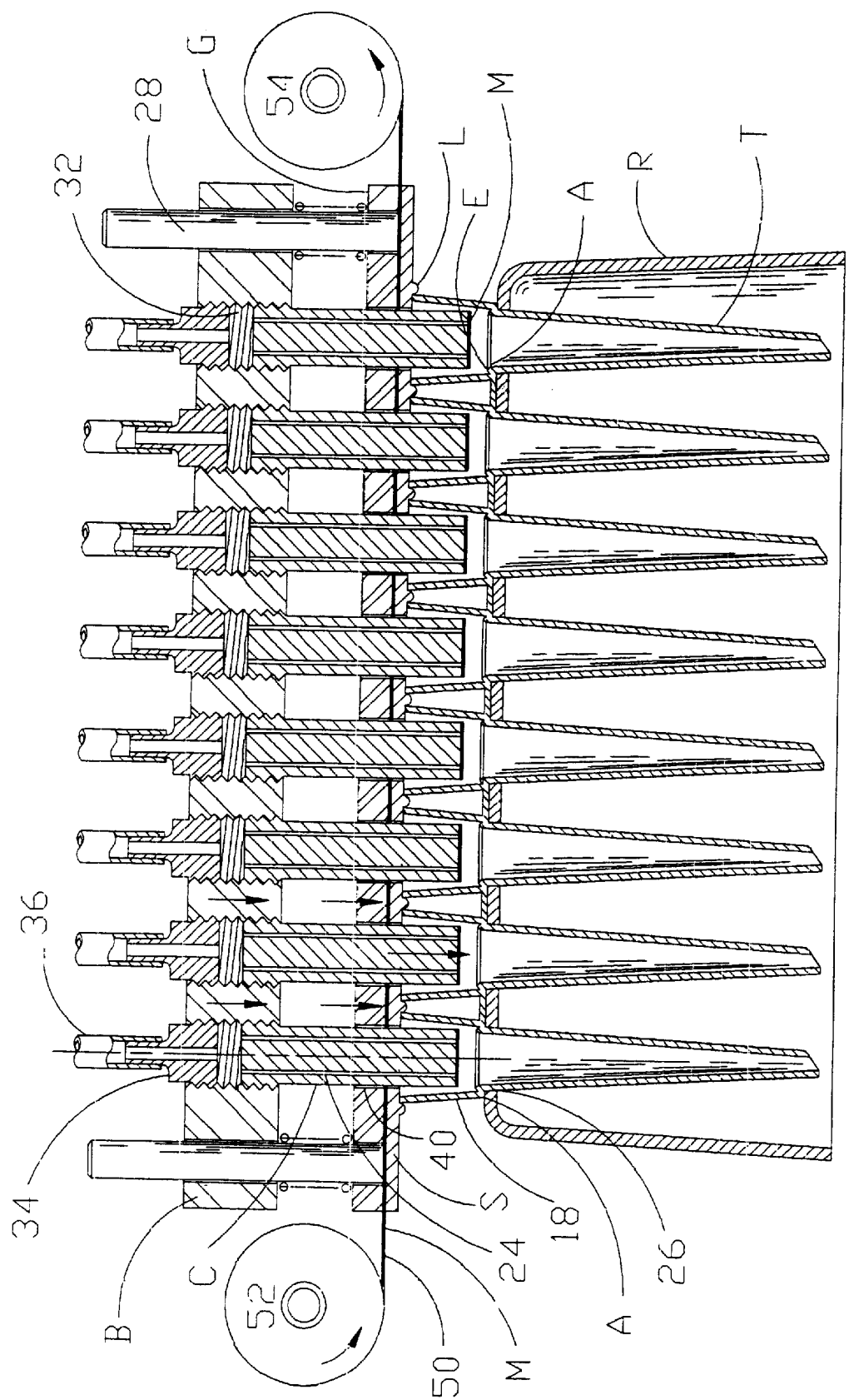
FIG. 6 illustrates the apparatus of FIG. 5 after punching has occurred and immediately before placement of the membrane filter material to the pipettes occurs.
Figure 7:
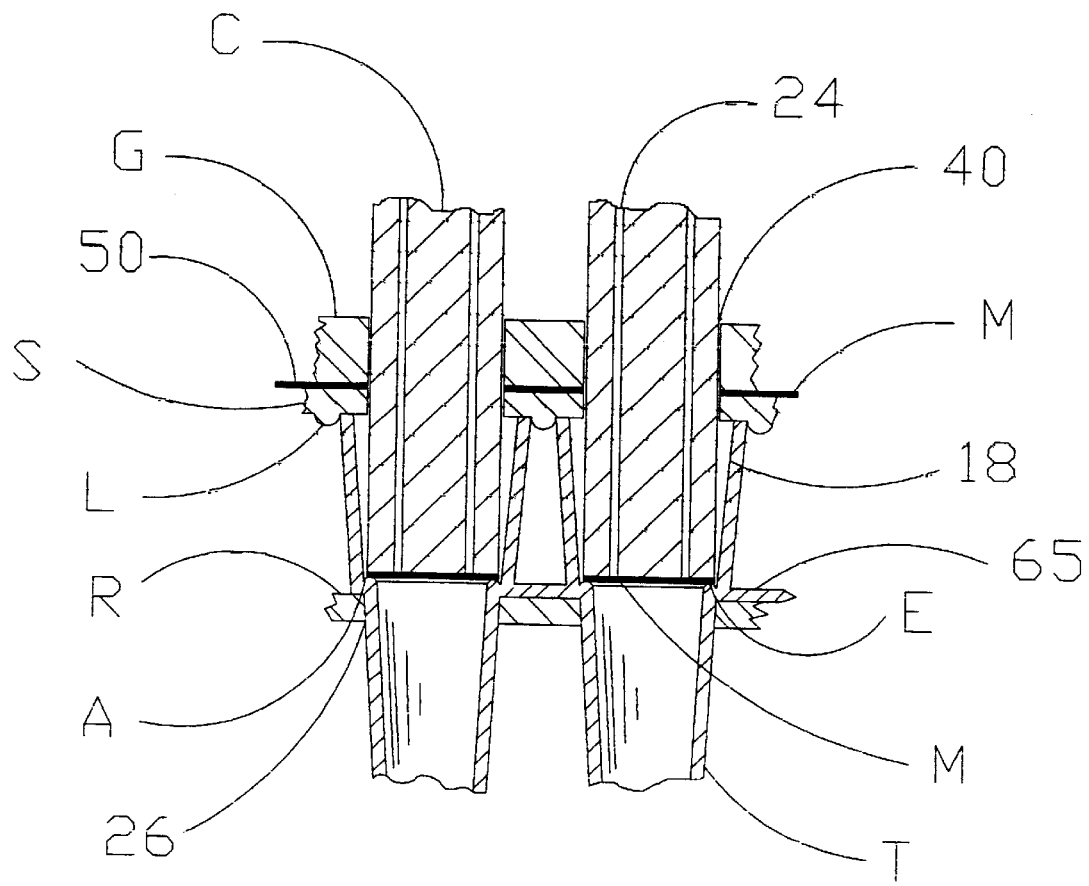
FIG. 7 is a detail of the apparatus of FIG. 6 at the time of placement of the membrane filter to the pipette tip.

Existing filter tips are primarily hand assembled at this time and at great cost. However, it will be seen that the embodiments of FIGS. 5, 6 and 7 show techniques that could be used to hold, shear, locate, and seal the filtered material to groups of filter tips trays, thereby providing the ability to automate the high production needed for these disposable products.

The following is a theory of operation of a concept design which would allow filter membrane sheeting to be attached to groups of disposable tips and/or insertable membrane filtered cylinders.

Referring to FIG. 5, pipette tips T are placed in holding rack R at apertures 26. Placement or pipette tips T occurs to apertures 26 at the exterior of annulus A on each pipette tip.

As held in rack R, truncated base 18 is upwardly exposed to shear plate S between respective locators L. As will be seen, locators L precisely register pipette tips T for insertion of their respective membrane filters M. Thus, rack R is loaded (i.e., 8, 16, 24 . . . 96) and positioned under shear plate S.

Shear plate S includes vertical guide rods 28. On vertical guide rods 28 block B has respective threaded apertures 32. Attached to the lower end of threaded apertures 32 is heated cylinder C. Attached to the upper end of threaded apertures 32 are vacuum connectors 36 to threaded connectors 34. Block B is heated so that heat may pass by conduction to heated cylinders C extending from heated block B.

Shear plate S includes defined punch apertures 40. Punch apertures 40 are the exact size of membrane filter M so that when heated cylinder C pass through punch apertures 40, membrane filter M can pass through dispensed filter material 50 passing between supply roll 52 and take up roll 54.

Having set forth the basic construction, operation can simply be set forth. Heated cylinder C is heated to approximately 300 degrees to 400 degrees Fahrenheit by heating heated block B. Filter membrane material is positioned over all disposable plastic tips by passing over the top surface of shear plate S immediately under heated cylinders C. Thereafter, heated block B downward thereby punching and carrying filter membranes M between it and shear plate S.

Referring to FIG. 6, immediately after punching membrane filters from M dispensed filter material 50, vacuum is communicated to vacuum connectors 36. Vacuum in each heated cylinder C holds severed membrane filter M in place as the respective heated cylinders C begins downward motion and carriers shear plate S on its advancing tip. Heated cylinders C (now holding sheared membrane disc with vacuum) move downward to mate with energy director E on pipette tips T.

The reader will note that vacuum may not be needed to hold disc in place during downward stroke since as heated cylinders move downward they pressurize the tip cavity where the air can only be released through the small orifice thus providing a force upward.

Referring to FIG. 7, heated cylinders C (preferably heated between 300–400 degrees Fahrenheit) now mates and applies pressure (i.e. 1–5 lbs.) to energy directors E on annulus A, of each pipette tips T for 1–3 seconds. Energy director E in turn melts and adheres filter media to plastic tip. A high temperature, non stick coating on the end of heated cylinder C that mates with the membrane would help to prevent membrane sticking.

Thereafter, vacuum releases at vacuum channels 24 through threaded connectors 34 and vacuum connectors 36. Heated cylinders C return to their original positions as shown in FIG. 5. Retainer plate releases punched filter membrane material for an incremental advance between supply roll 52 and take up roll 54.

Regarding such incremental advance, it will be recognized that dispenses filter material 50 need to advanced once every other stroke the full length of shear plate S. It is also understood that static eliminators are also helpful when cutting rolled material in this manner. This dispensed filter material 50 can advance only the amount interstitial distance between punch apertures 40 so that maximum and efficient material extraction occurs from dispensed filter material 50. A rack R is installed similarly loaded with pipette tips T.

By utilizing thin membrane sheet in roll stock and automating the procedure to heat stake the filter media to each tip or cylinder in groups of up to 96 at a time, the cost of the assembly can be greatly reduced over that of existing filter tips while providing a superior product.

It is also understood that filter tips that do not require secondary reagent or reactive coatings could also be manufactured using an insert injection molding method known in the art. This method would permit the filter material to be inserted into the injection mold at the same time, when the plastic tips are being formed. Depending on the filter tip configuration, this tooling can require one cavity with multiple cores. The first core may be used to help form the lower plastic portion of the tip below the membrane during the first stage of injection, while a second core would be required to form the upper section of the tip, while locating the filter material and completing the part as a one piece molded assembly. It is also noted using spring loaded shutoff pins to guard against crushing the membrane roll stock and multiple cauitation (i.e. 2, 4, 8, 12, etc.) will be incorporated to automate and increase the productivity of the tooling.

Many types of filter membrane materials can be manufactured and installed using these techniques. Depending upon the application, environment, and the need, a custom filter can be manufactured to meet the new and demanding technology of tomorrow (i.e., DNA and PCR procedures, etc.). Having the ability to modify the roll media membrane, while keeping the tips and manufacturing process the same, creates several opportunities to design various filter and media for specific applications or needs.

Because of reduction in filter mass, the new thin filter membrane concept could be used for very small pipette tips (i.e., 0.5 to 50 $\mu$l). This area has been dominated by the new positive displacement tips which provide both a plastic piston and tip to prevent cross-contamination between samples. Using filter membrane disposable tips (as shown in FIG. 4) could allow air-interface pipetters to compete with positive displacement pipetters and still provide the safety from cross-contamination at a much reduced cost.

While developing the concept of filter membrane pipette tips, I also discovered a similar need in the multichannel pipetter area, which is outlined in my Invention Disclosure "Multichannel Filtered Pipette Tips" dated Nov. 26, 1995. The multichannel pipetters were developed primarily to increase the number of dispensings one was capable of doing at one time. In most cases, the multichannel pipetters are designed to hold either 8 or 12 individual pipette tips, due to the fact that their primary use is to fill or remove fluid from a standard 96 (8×12) microwell plate on 9 mm centers. These tips are individually manufactured and packaged in tip trays of 96 (0.354 center to center) and are used for both the single use pipetters and multichannel alike. If a need arises for a filter tip, then you purchase a standard tray of 96 tips that have had 96 plug filters pressed into their cavities, thus requiring 192 individual pieces (96 tips and 96 filter plugs) to manufacture a standard 8×12 filter tip tray. My new invention, as outlined above, reduces the number of parts necessary to create a similar tip tray while also increasing its filter capability by incorporating a sterilizing filter membrane which provides an effluent in which no microorganisms are demonstrable.

Figures 8, 9:
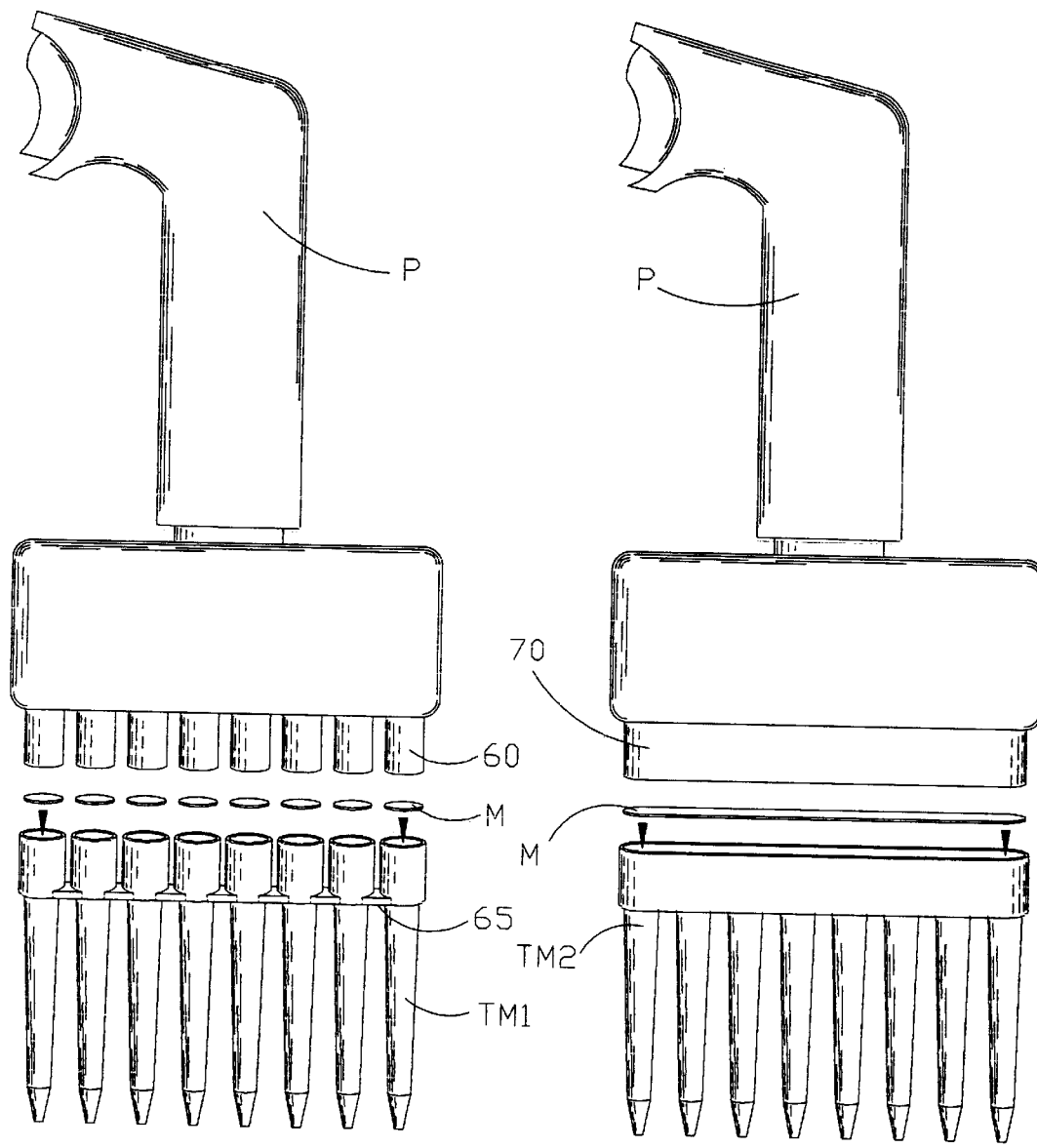
FIG. 8 illustrates a multiple pipette tip where the respective pipette tips are each independently mounted.
FIG. 9 illustrates a multiple pipette tip where the respective pipette tips are all integrally mounted.

The combining of many individual tips into one part creates the following advantages:

FIG. 8 shows a lower portion of standard 8 channel pipetter similar to those manufactured by Oxford, Brinkman, Fisher, etc. These multichannel pipetters have adjustable volumes usually ranging from 5 $\mu$l to 200 $\mu$l in increments of 1 $\mu$l with accuracy to 1.0% and precision to less than or equal to 0.5%. These multichannel pipetters work very similar to the regular pipetter with the exception that it will pick up and dispense 8 to 12 individual tips at one time. In FIG. 8, pipette tips Tm1 are all molded together and all attached to pipette P having individual pipetting outlets 60 for each of the multiple tips.

FIG. 9 shows 8 tips molded in a one piece at pipette tips TM2.

Figure 10A:
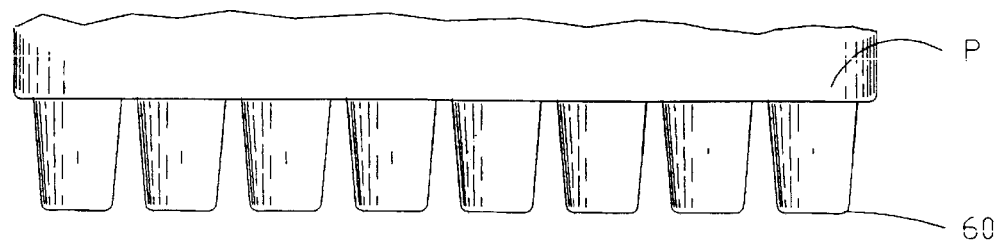
FIGS. 10A, 10B and 10C are respective side elevation, plan, and side elevation sectional views of a first type of multiple pipetter tip.
Figure 10B:
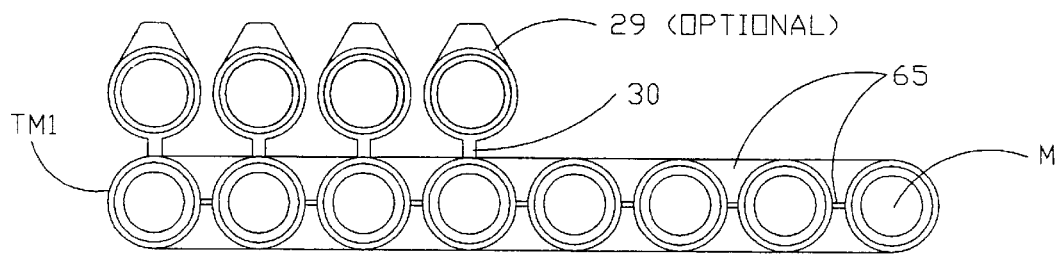
Figure 10C:
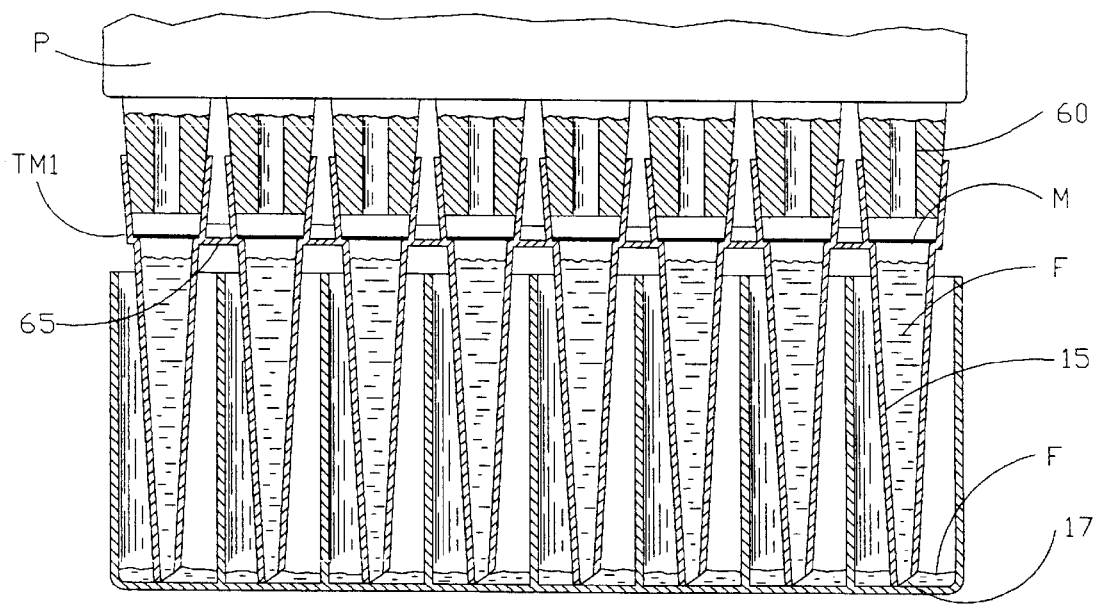

Referring to FIGS. 10A–10C, it will be observed that individual pipetting outlets 60 connect to pipette tips TM1. These respective pipette tips TM1 are configured with individual energy directors E molded in to facilitate the heat or sonic welding of the thin microporous membrane. It is also understood that the membrane filter maybe insert injection molded as described earlier. In either case by manufacturing this as a one piece assembly it is possible to consolidate the number of parts to fill a tip tray from 96 individual parts to 12 if 8 tips are molded together or 8 if a 12 tips cavity tool is used. This decreases the piece part price while also decreases the labor costs involved in packaging which is usually done by hand.

FIG. 10B shows a plan view of FIG. 10C with thin ribs 65 being constructed between the individual tips as to position them for attachment to the multichannel pipetter. The mating of each barrel with the inside surface of each tip creates a surface to surface seal for functioning.

Figure 11A:
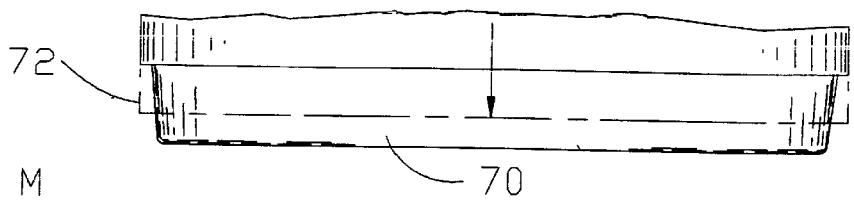
FIGS. 11A, 11B and 11C are respective side elevation, plan and side elevation sectional views of a second type of multiple pipetter tip.
Figure 11B:
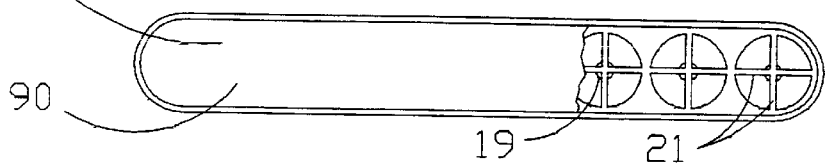
Figure 11C:
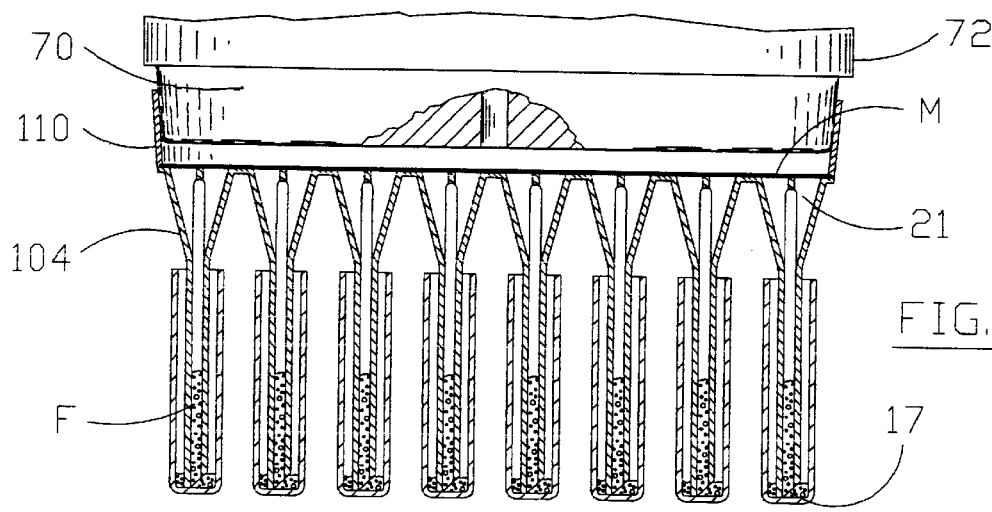

FIGS. 11A–11C shows an alternate design to molding multiple cylinder diameters to mate with existing multichannel pipetters. This new design consists of only one pipetter barrel 70 that would replace the multiple barrels seen in FIGS. 10A–10C. The multiple tip configuration would then be manufactured to make only one sealing surface for mating with pipetter barrel 70. This is shown in broken lines in FIG. 11C as a partial section. This is unlike existing art which would require 8 or 12 individual sealing diameters to accomplish the same end result, thus being less costly to manufacture.

It will be understood that FIGS. 8 and 9 combined with FIG. 11C illustrate a different method of manufacture from the energy director E previously utilized. This method of manufacture is shown in detail in FIGS. 17A–17D.

Referring to FIG. 17A, conical female mold section 100 has first shuttle male mold section 102 engaged and centered. Thereafter, bottom conical section 104 with shoulder 106 is molded.

As shown in FIG. 17B, once this molding has occurred, first shuttle male mold section 102 is removed exposing bottom conical section 104 and shoulder 106. Thereafter, membrane M is placed, utilizing a process similar to that previously illustrated in FIGS. 5–7. With the membrane M in place, second shuttle mold section 108 then occupies and overlies the previously molded part and membrane filter. As shown in FIG. 17D, molding of upper pipette tip 110 occurs, fusing bottom conical section 104 to upper pipette tip 110.

Referring briefly to FIG. 11C, the same sequence of fabrication is shown. Specifically, a first injection does tips T; a second injection forms pipetter barrel 70, trapping membrane M therebetween. Again, the order of the molding can be reversed.

It can be readily understood that the illustrated molds of FIGS. 17A–17D can be easily adapted to the process shown in FIGS. 5–7.

It will be understood that I here illustrate the technique of fusing membrane M to pipette tips grouped together. It will be as well understood that individual fusing of the pipette tips in the singular manufacture of pipette tips will work as well.

Additionally, it will be understood that both disclosed methods of tip manufacture have their own usefulness. For example, where it is desired to coat the interior of the pipette with reagent or reactant coatings for interacting with the contents of the pipette, the attachment of the membrane utilizing energy director E is preferred. This gives the least amount of interference from the fabrication process to the placement of membrane M.

Alternately, where coating of the interior of pipette tip is not desired, fusing of membrane M across portions of the pipette is preferred.

Referring to FIGS. 11A–11C, it will be seen that the filter media can be manufactured in strips 90 as shown and heat or sonic welded to the multiple tips by using energy directors E in one operation. This again reduces the number of components necessary to make a standard filter tip tray. As previously discussed, the existing art uses 96 individual tips and 96 individual filter plugs. This new design can replace 192 parts with as few as 16 total parts using a 12 tip configuration or 8 parts if the multiple filter tips are insert injection molded as one piece assemblies, as mentioned earlier. The multiple tips would still attach very similar to existing multichannel pipetter except as one piece assembly requiring only one sealing ring. This seal could also be made by incorporating an elastomer O-ring type seal on the pipetter barrel to facilitate any tolerance misalignment of the two mating parts. Because the filter media would prevent any contaminates from reaching the barrel 70 there would be no problems with cross-contamination between parts. In addition, the tip assemblies would be able to be installed by normal means (press fit) and removed similar to existing tips with the use of an ejector sleeve schematically shown as ejector 72 in FIGS. 11A and 11B. These multiple tip configurations (i.e., 2, 4, 8, 12, etc.) could also incorporate the use of dry reagent coatings, protective caps and tip caps for the storage or testing of fluids.

As previously described, the filter membrane should never contact any fluid drawn within each tip. With existing adjustable volume multichannel pipetters the ranges run from 5–50 μl and 50–200 μl. The maximum volume in each case would be 50 and 200 μl respectively. Therefore, the tips maximum volume would be designed to hold approximately 15 to 20% more (i.e. 60 μl & 240 μl) to ensure no contact occurs. This is because of the possible fluid migration that might occur between tips (cross-talk) when a single sheet of filter membrane would be used instead of an individual disc.

Figure 12:
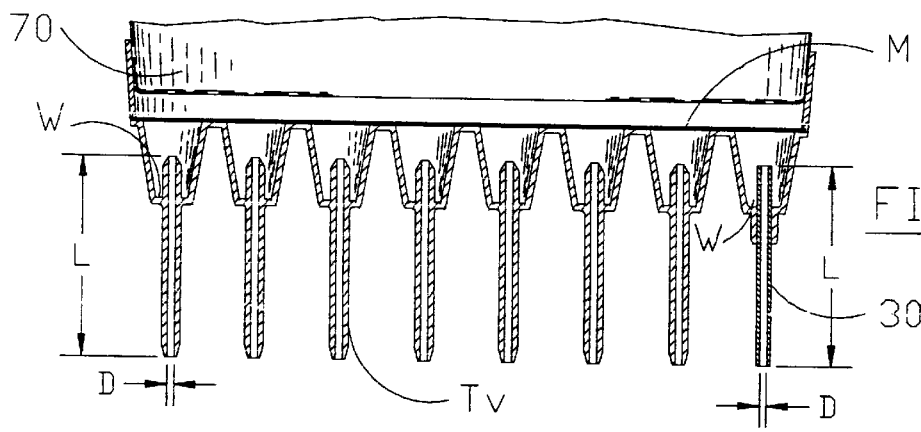
FIG. 12 is a side elevation section similar to the side elevation sections of FIGS. 10C and 11C illustrating a multiple pipette tip with attached well for precision volume multiple pipetting.
Figure 13:
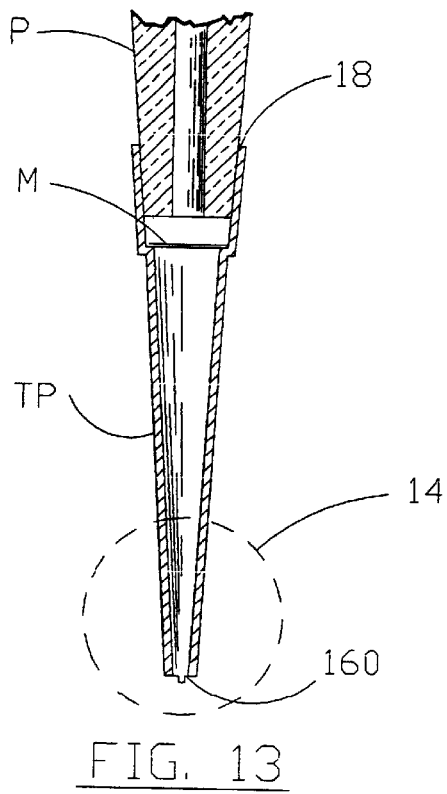
FIG. 13 is a side elevation section of an improved tip according to this invention illustrating a modified tip point for collecting the bottom adjacent portions of sample within a sample vial.
Figure 14:
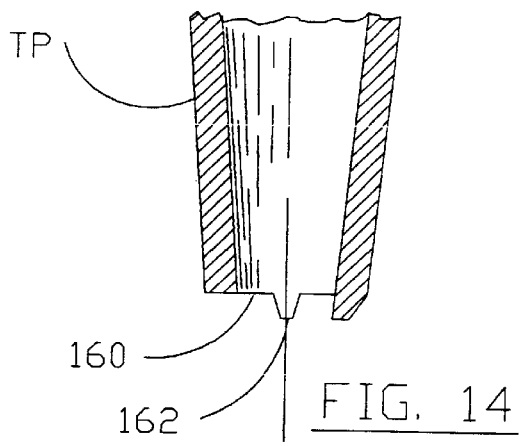
FIG. 14 is an expanded view of the tip of FIG. 13.
Figure 15:
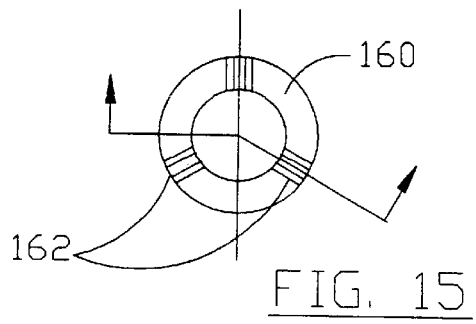
FIG. 15 is a bottom plan view of FIG. 14 showing in the illustrated section lines the portions along which the section is taken.

In another variation of multiple tip design, FIG. 12 shows an assembled pipetter barrel mating and sealing with 8 filter tips TV. These tips are designed to hold a particular pre-calculated volume of any viscosity liquid. The diameter d and length l is predetermined in the injection mold or manufactured as a separate needle or tube then mechanically attached to the plastic hub to produce a specific volume of fluid when the fluid is drawn into the tip. NOTE: This method even though more costly allows for very small I.D. in the range of 0.005 to 0.007 in diameter over considerable length, which would be impossible with injection, but yet needed when dispensing small amounts of fluid (i.e., 0.5 to 5 μl). When the specific volume is reached, the top of the column acts as an overflow which allows the fluid to overflow into well W below it. When the maximum volume is reached, the tip is withdrawn from its reservoir and then it dispenses only that fluid which is calibrated by volume within diameter d over its length l. The barrel is again protected from any fluid, gas or aerosol by the filter membrane 90.

This concept would work well using existing single or multichannel pipetters by creating a specific volume of tip, say 30μ., then by setting the desired volume to say 33 μl or 110%. The additional 3 μl would overflow into the well W if the accuracy of the instrument was correct. Some of the benefits of this technology compared to the air displacement pipetting systems alone are the following:

Tips are calibrated in the injection mold. The volume taken in is unaffected by atmosphere pressures. Further, the volume pipetted is unaffected by temperature variations. Further, the volume is unaffected by user technique. Again the filter media can be applied in strip form or individual discs as shown if so desired to provide the improved microfiltrations needed in today's increasingly demanding biotechnology and pharmaceutical markets.

Figure 16:
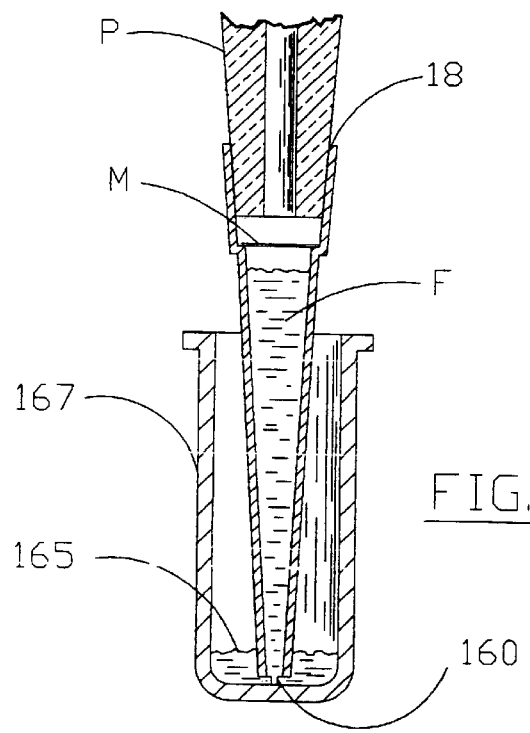
FIG. 16 illustrates the tip of FIG. 13 within a vial about to extract the bottom adjacent portions of sample from the vial.

Referring to FIGS. 13–16, an improved tip 160 is illustrated. Referring to the section line illustrated in FIG. 15 and the side elevation section of FIG. 14, it will be seen that collection channels 160 are formed between tip feet 162. As illustrated in FIG. 16, this construction has the advantage of being able to collect the last remaining portions of sample 165 from a vial 167. This occurs because discrete channels are formed between the bottom of vial 167 and collection channels 160.

What is claimed is:

1. A pipette tip comprising in combination:
   a pipette tip body defining at least one interior frustum shaped cavity having an apex end for receiving fluid and a base for attachment to a pipetter;
   a body within the pipette tip body defining an annulus about the interior frustum shaped cavity;
   the annulus set off from die wall of the frustum cavity and exposed to the base of the pipette tip body;

a first membrane filter attached to the annulus within the pipette tip body and extending across the pipette tip; and, a second membrane filter mounted to the body within the pipette tip body below the first membrane filter to define a volume between the first and second membrane filter.

2. A pipette tip according to claim 1 and wherein:

the second membrane filter being attached to the pipette tip body at an annulus below the first membrane.

3. A pipette tip according to claim 1 and wherein:

the apex end of the pipette tip body being symmetrical around an axis; and, the apex end of the pipette tip body being truncated at an angle with respect to the axis.

4. A pipette tip according to claim 1 and wherein:

the second membrane filter mounted below the first membrane filter confines reagents and/or reactants to the volume between the first and second membrane filter.

5. The combination of claim 1 wherein the pipette tip further includes:

a first cap for closing the base of the pipette tip when the pipette tip is removed from the pipette device; and, a second cap for closing the apex end whereby the pipette tip can be used as a fluid container.

6. The combination according to claim 1 wherein:

the second filter membrane is impregnated with substances that will react to fluid as it flows through the filter.

7. The combination according to claim 1 wherein the pipette tip body is coated with a reagent and/or reactant.

8. The combination according to claim 1 further comprising:

a tube mounted to the apex end of the pipette tip.

* * * * *